United States Patent

Zech et al.

[11] Patent Number: 5,849,812
[45] Date of Patent: Dec. 15, 1998

[54] ADDITION-CROSSLINKING POLYETHER IMPRESSION MATERIAL

[75] Inventors: Joachim Zech, Hechendorf; Erich Wanek, Kaufering, both of Germany

[73] Assignee: Thera Patent GmbH & Co. KG Gesellschaft fur Industrielle Schutzrechte, Seefeld, Germany

[21] Appl. No.: 852,904

[22] Filed: May 9, 1997

[30] Foreign Application Priority Data

May 9, 1996 [DE] Germany ............... 196 18 719.2

[51] Int. Cl.$^6$ ............... C08L 71/00; C08L 71/02; C08K 5/24; A61C 9/00
[52] U.S. Cl. ............... 523/107; 524/413; 524/448; 524/506
[58] Field of Search ............... 523/109; 524/506, 524/413, 448

[56] References Cited

U.S. PATENT DOCUMENTS

| 3,453,242 | 7/1969 | Schmitt et al. |
| 4,093,555 | 6/1978 | Schmitt et al. |
| 4,167,618 | 9/1979 | Schmitt et al. |
| 5,138,009 | 8/1992 | Inoue. |
| 5,637,628 | 6/1997 | Kamohara et al. ............... 523/109 |

FOREIGN PATENT DOCUMENTS

| 31 02196 | 1/1981 | Germany. |
| 34 23823 | 6/1984 | Germany. |
| 3741575 | 6/1988 | Germany. |
| 39 02817 | 1/1989 | Germany. |
| 39 13250 | 4/1989 | Germany. |
| 39 13252 | 4/1989 | Germany. |
| 3838587 | 5/1990 | Germany. |
| 4010281 | 10/1990 | Germany. |
| 41 23946 | 7/1991 | Germany. |
| 4019249 | 8/1991 | Germany. |
| 41 29613 | 9/1991 | Germany. |
| 43 0.6997 | 3/1993 | Germany. |
| 43 32037 | 9/1993 | Germany. |

*Primary Examiner*—Nathan M. Nutter
*Attorney, Agent, or Firm*—Birch, Stewart, Kolasch & Birch, LLP

[57] ABSTRACT

An addition-crosslinking polyether impression material is described which contains (a) at least one polyether which has at least two optionally substituted vinyl and/or allyl end-groups,
(b) an SiH component,
(c) at least one platinum catalyst,
(d) optionally usual additives, and
(e) an organopolysiloxane with at least two alkenyl groups.

The impression material has in at least two-part form of administration in which the components (b) and (c) are spatially separated from each other a particularly satisfactory storage stability and has good mechanical properties in the cured state.

21 Claims, No Drawings

ADDITION-CROSSLINKING POLYETHER IMPRESSION MATERIAL

The most important prerequisite for producing dentures in the dental laboratory is a working model which reproduces the patient's tooth and jaw conditions as faithfully as possible. For this, a negative mould is firstly made in the patient's mouth by the dentist using so-called impression materials. The initially plastically mouldable impression material is introduced into the patient's mouth using an impression cup and solidifies there to give as elastic a material as possible which, after removal, represents the negative mould. This mould can then be filled with a modelling material and thus leads to the working model.

High-precision elastic impression materials, which are characterized by high impression accuracy, high shape retention and good detail reproduction are, for example, materials based on agar-agar, polysulphides, polyethers or the addition-crosslinking silicones. In the case of the polyether materials, aziridine-containing substances are polymerized as are described e.g. in U.S. Pat. Nos. 3,453,242 and 4,093,555 or also in DE-A-43 06 997. Normally, fillers, dyes and further auxiliaries are also used in addition to the aziridine-containing compounds. The sulphonium salts known from U.S. Pat. No. 4,167,618 are very suitable for initialing the polymerization reactions. On account of their hydrophilic behaviour, the polyether materials are predestined to record the tooth situation in the mouth as exactly as possible, even in the moist oral environment, through good flow on behaviour.

In the case of the addition-crosslinking silicone impression materials, the curing is achieved by reaction of a polysiloxane having vinyl end-groups with a polysiloxane having SiH groups by means of particular platinum catalysts. The impressions obtained in this way are characterized by very good elastic properties and high storage stabilities. On the other hand, the accuracy of reproduction can only be described as good to a limited extent, because of the hydrophobic character of the silicones.

In order to improve the hydrophilic behaviour of silicone impression materials, it has thus been proposed to add hydrophilizing additives to the addition-crosslinking silicone impression materials. These additives bring about an improvement in the contact angle of a drop of water on the impression material. In the case of addition-crosslinking silicone impression compositions, the better wettability is, however, also associated with an increased water absorption on contact with moist media, which can result in a worsened dimensional stability and increased evolution of hydrogen. Moreover, the effect of the reduction in the contact angle in hydrophilized silicones is lost again in the course of single or repeated disinfection.

Compared with silicones, addition-crosslinking polyether impression compositions as described e.g. in DE-A-37 41 575, DE-A-40 19 249, DE-A-40 10 281 and in DE A 38 38 587 bring with them an improvement in the hydrophilic properties. A curing reaction takes place here based on a platinum-catalysed addition reaction of a SiH component with an unsaturated polyether. In contrast to addition-crosslinking silicones, this is generally the main component and gives the matrix a hydrophilic characteristic.

Described in DE-A-37 41 575 are curable impression materials which, in addition to unsaturated polyethers with terminal alkenyl radicals, also contain the reaction products of such substituted polyethers with oligosiloxane radicals having at least two SiH groups in the molecule and platinum catalysts as the main constituents. They are to be used as tooth impression material and have good elastic and strongly hydrophilic properties.

Similar compositions are described in DE-A-40 19 249, in which a silicone oil with a viscosity of below 10,000 $mm^2/sec$ is added to improve curability under moist conditions and a polyvinyl ether is added to improve contact pressure.

Application DE-A-40 10 281 describes impression compositions containing a polyether polymer with at least two alkenyl groups in the molecule, a polyorganohydrogen siloxane with at least three SiH groups in the molecule, a platinum catalyst, inorganic filler and an antioxidant. In order to improve the compatibility and the reactivity of the SiH groups-containing polysiloxane with the unsaturated polyether polymer, it is proposed either to substitute the polyorganohydrogen siloxane with polyether radicals, or to attach vinyl siloxane or vinylsilyl and end-groups to the alkenyl group-containing polyether polymer.

DE-A 38 38 587 describes impression materials which consist of at least one polyether which has at least two optionally substituted vinyl and/or allyl end-groups, of an SiH component, of at least one platinum catalyst and optionally usual additives, the SiH component being obtainable from an allyl or vinyl hydrocarbon compound with at least one aromatic, unsaturated, heterocyclic or cycloaliphatic ring and at least one difunctional SiH compound.

It is necessary for the dentist to have available in his practice an impression composition which is storable and the usability of which is guaranteed over a period of from several months to years. A form of administration of the above-described materials in a one-component paste formulation is therefore not possible since curing of the paste would quickly take place in the course of storage. It is therefore necessary to separate spatially from one another the reactive constituents in the formulation—the SiH-containing component, the unsaturated polyether polymer and the platinum catalyst. The SiH component and the platinum catalyst required for curing at room temperature cannot be combined in a paste since this would result in decomposition of the SiH component. A two-component formulation is therefore described in the state of the art, in which a mixture of the SiH-containing component and the unsaturated polyether are contained in one paste and the platinum catalyst together with the unsaturated polyether are contained in a second paste. Immediately before application in the dentist's practice, the two pastes are mixed together and cure after they have been introduced into the mouth of the patient.

However, in the course of storage over a period of several weeks to months, the problem arises that a catalyst paste in which the platinum catalyst is present together with the unsaturated polyether also does not exhibit satisfactory storage stability. This is shown, for example, in a continuous slowing down of the vulcanization reaction after the two pastes have been mixed together which becomes all the more apparent the longer the paste containing the platinum catalyst is stored, under after some time vulcanization is no longer possible. This is presumably to be attributed to the sensitive platinum catalyst in the mixture with the polyether being slowly damaged, in particular when common platinum complexes are used, such as e.g. platinum-vinyl siloxane complexes. DE-A-40 10 281 therefore proposes adding antioxidants to increase storage stability. However, this achieves only an unsatisfactory long-term storage stability.

It is the object of the invention to provide an elastic addition-crosslinking polyether impression material which is stable on storage in the formulation of the pastes and which also has an adequate storage stability in the form of the cured impressions and good mechanical properties.

This object is achieved by an addition crosslinking polyether impression material which contains (a) at least one polyether which has at least two optionally substituted vinyl and/or allyl end-groups, (b) an SiH component, (c) at least one platinum catalyst, and optionally (d) usual additives and which is characterized in that it additionally has (e) an organopolysiloxane with at least two alkenyl groups.

The impression material according to the invention has the advantage that a two-component form of administration is made possible, in which the platinum catalyst (c) together with the component (e) as a paste base in a so-called catalyst paste has an excellent long-term storage stability, and in which separation of the polyether (a) and of the platinum catalyst (c) can take place.

The usability of organopolysiloxanes with at least two alkenyl groups in the impression compositions according to the invention for the production of dimensionally stable and elastic impressions is surprising. It is described in the literature that foam-rubber-like products with unsatisfactory mechanical properties result when SiH-containing polysiloxanes are cured with alkenyl group-containing polyethers in the presence of a platinum catalyst (see Journal of Polymer Science: Part A: Polymer Chemistry, Vol. 31, 1993, p. 2617). The reason for this lies in the general immiscibility of the two components with each other, which results in a separation and/or incomplete setting of the material. DE-A-37 41 575 explains on p. 4, lines 9–22 that a precise impression cannot be produced when tooth impression compositions are used which contain a polyether with alkenyl radicals, a polyorganohydrogen siloxane with a H-Si group, and a complex platinum catalyst. The reason for this is the poor compatibility between the polyether and the polyorganosiloxane, the result being that a completely cured body can scarcely be obtained. It therefore had to be feared that the combination of a hydrophilic polyether component (a) and a hydrophobic organopolysiloxane component (e) will likewise result in separation problems during the curing reaction and that incorporation of component (e) will not take place. Surprisingly, however, precise, elastic and dimensionally stable rubbers with good mechanical properties result when the impression compositions according to the invention are cured, although two completely incompatible components are mixed together, which contradicts the teaching of the cited literature.

There were indeed similar compositions in the state of the art. Thus DE-A-40 19 249 and DE-A-40 10 281 describe the possibility of adding silicone oils to special addition-crosslinking impression compositions containing unsaturated polyethers. In both cases, however, the silicone oil served other purposes, namely to disturb the network. A suggestion to obtain moulds which have good mechanical properties and are improved compared to using silicone oils, by means of a targeted addition of an organopolysiloxane with at least two alkenyl groups, cannot be inferred from the state of the art.

In the preferred two-component version of the polyether impression material according to the invention, components (a) and (b) are present in a so-called base paste, whereas components (c) and (e) are present in the catalyst paste. It is, however, also conceivable for at least part of component (e) to be present in the base paste or for at least part of component (a) to be present in the catalyst paste. However, the impression material according to the invention can also be constituted in such a way that all the components (a), (b), (c), (e) are present spatially separated. Furthermore, all three-component versions in which the components (b) and (c) are present spatially separated are also conceivable. The optionally present usual additives according to component (d) can be added to any other component or distributed over it.

A further subject is the use of the abovementioned addition-crosslinking polyether impression materials for producing dimensionally stable jaw impressions.

The di- or polyallyl ethers of polyether di- or polyols can for example be used as unsaturated polyethers (a). The polymers of ethylene and propylene oxide, copolymers of ethylene and propylene oxide and copolymers of ethylene oxide and tetrahydrofuran can for example be used as the polyether middle section. The polyetherdiols obtained from this can then be reacted e.g. with allyl or also vinyl chloride in a manner known per se to give the unsaturated polyethers (a). The unsaturated polyethers preferably have average molecular weights of 1000–20,000, particularly preferably of 1500 10,000 quite particularly preferably of 2000–7000. Suitable unsaturated polyethers are described in the aforementioned DE-A-37 41 575, the disclosure of which in this respect is to be included here.

Component (b) of the impression material according to the invention is a hydrocarbon or polyether compound, substituted by siloxane radicals, having at least 2 SiH groups in the molecule. The structure and method of production of these compounds are described inter alia in DE-A-38 38 587, DE-A-37 41 575 and DE-A-40 19 242. The disclosure of these publications in this respect is to be included here. Preferred components (b) are the SiH components described in DE-A-38 38 587, which are characterized in that they are obtainable by reacting an at least bifunctional allyl or vinyl hydrocarbon compound, the hydrocarbon radical of which, without taking into account that allyl or vinyl groups and optionally present alkylene ether groups, has 6–30C atoms and contains at least one aromatically unsaturated, heterocyclic or cycloaliphatic ring, with at least one mol per vinyl or allyl group of an at least bifunctional SiH compound of the formulae I or II.

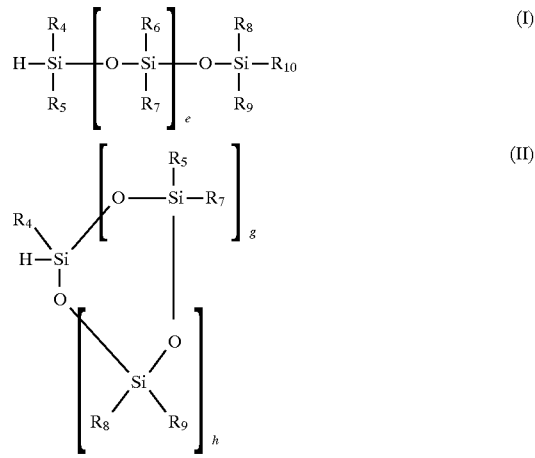

in which e=0–8, g=0–8, h=0–4 and $R^4$ to $R^{10}$, which can be the same or different, stand for H, methyl, phenyl or ethyl, where at least one of the radicals $R^4$ to $R^{10}$ and at most 5 of these radicals stand for H, and g and h cannot be 0 at the same time.

Going beyond the teaching of DE-A-38 38 587, the at least bifunctional SiH compound can also be a compound of the formula (III)

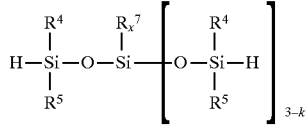 (III)

in which k may be 0 or 1 and $R^4$, $R^5$ and $R^7$ are as defined above.

The allyl or vinyl hydrocarbon compound is preferably an allyl ether, vinyl ether, allyl ester or vinyl ester hydrocarbon compound.

The SiH compounds preferably have the formula

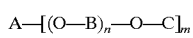

in which

A stands for a straight-chain or branched 2–6-valent hydrocarbon radical having 6–30C atoms, containing at least one aromatically unsaturated or cycloaliphatic ring, B stand for a straight-chain or branched saturated hydrocarbon radical having 2-0C atoms, m=2–6, n-0–25 and C stands for the radicals

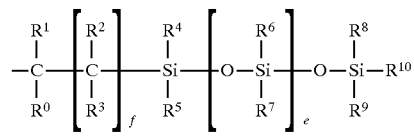

or

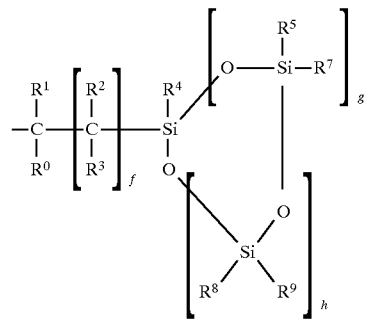

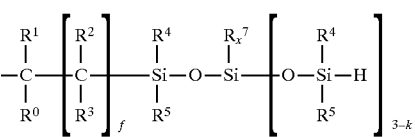

or

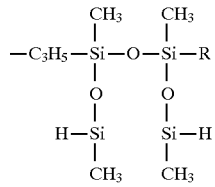

where $R^0$–$R^3$, which can be the same or different, stand for H, methyl or ethyl, and f=1 or 2, and e, g, h and k, and $R^4$–$R^{10}$, have the above meaning.

In the above formula for the SiH compound, the radical A is preferably a divalent 1,4 phenylene, 2,7-naphthylene, 4,4-isopropylidene diphenylene, 4,4'-biphenylene, phthaloyl, terephthaloyl or tricyclo[5.2.1.0$^{2,6}$]decane-3,8-dimethylene radical. Radical B is preferably an ethylene or a propylene radical, m is preferably 2–4, particularly preferably 2, n is preferably 0–10, particularly preferably 0–3. In radical C, the radicals $R^0$–$R^3$ are preferably H or methyl, particularly preferably 11, and the radicals are the same. f is preferably 2, $R^4$ and $R^5$ are preferably methyl. $R^6$ is preferably H, $R^7$ and $R^9$ are preferably methyl, $R^8$ is preferably H or methyl. $R^{10}$ is preferably H or Me. e is preferably 0–5, particularly 1–3. g is preferably 1–4, and h is preferably 1–2. k is preferably 0. The radicals C particularly preferably represent the following formulae:

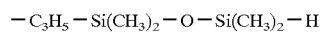

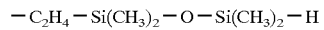

$$-C_3H_5-\underset{\underset{O}{|}}{\underset{|}{Si}}-\underset{CH_3}{\overset{CH_3}{|}}-O-\underset{\underset{O}{|}}{\underset{|}{Si}}-\underset{CH_3}{\overset{CH_3}{|}}-R$$

$$H-Si\quad Si-H$$
$$|\quad\quad |$$
$$CH_3\quad CH_3$$

R = H, CH$_3$

Particularly preferred are compounds of the following formulae: (n=0, 1, 2 or 3)

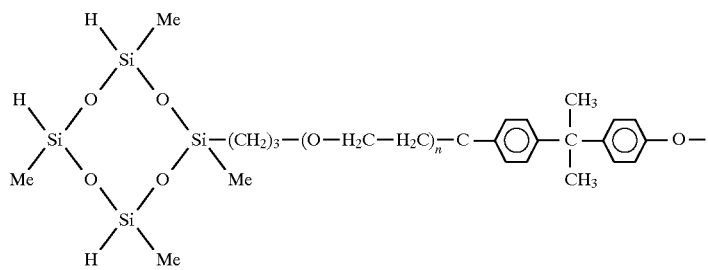

I.

-continued

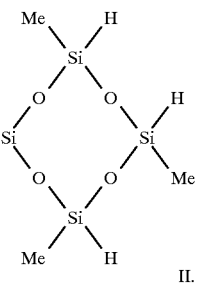
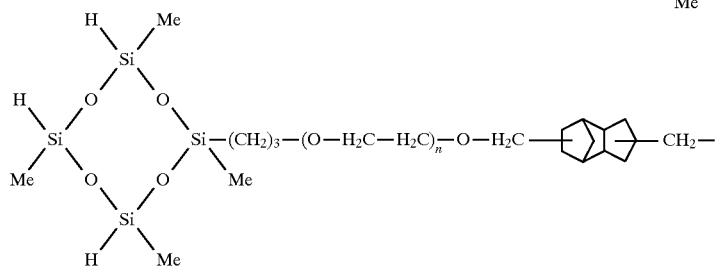

II.

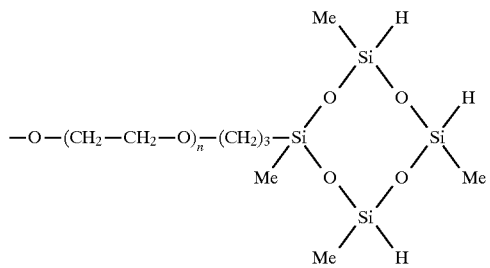

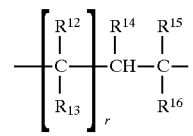

The siloxane-substituted aromatic or cycloaliphatic compounds can be produced according to conventional methods or also analogously to DE-A-37 41 575 or analogously to DE-A-38 38 587. Production expediently takes place by reacting a di- or polyallyl- or -vinyl aromatic compound with a polyorganosiloxane which contains at least 2 SiH groups, using a platinum catalyst in a molar ratio of at least 2 SiH groups to one allyl or vinyl group. Suitable starting substances are for example the diallyl ethers of bisphenol A, of ethoxylated bisphenol A and of bishydroxymethyltricyclo [5.2.1.0$^{2,6}$]decane and also the diallyl esters of phthalic and terephthalic acids. The catalyst used must be removed to produce storage-stable pastes, which can suitably take place by adsorption of silica gel, diatomaceous earth or the like.

Also suitable as component (b) are the unbranched or branched siloxane-substituted polyethers described respectively in DE-A-37 41 575 and DE-A-40 19 249 with regard to their structure and production and having terminal polyorganosiloxane radicals and at least two SiH groups in the molecule which have the following general formula:

$$D\{(-O-R^{11})_p-O-E-G\}_q. \quad (IV)$$

in this case, D stands for a di- to hexavalent, preferably di- or trivalent, saturated hydrocarbon radical with 1 to 10 carbon atoms, preferably 2 to 4 carbon atoms, $R^{11}$ stands for an unbranched or branched alkylene radical with 1 to 6 carbon atoms, preferably with 2 to 4 carbon atoms, with the proviso that when p stands for the number 2 or a larger number, the radicals $R^{11}$ are the same or different. p stands for a whole number from 1 to 30, preferably 1 to 10, q stands for a whole number from 2 to 6, preferably 2 or 3. The chain composed of the units —O—$R^{11}$— can be a statistical polymer or a block copolymer.

In the general formula (IV) the radicals E are identical or different alkylene radicals of the formula (V)

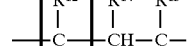

in which $R^{12}$ to $R^{16}$ are the same or different and in each case stand for a hydrogen atom or an alkyl radical with 1 to 10 carbon atoms, and r is a whole number from 1 to 10.

If in the last-mentioned formula the radicals $R^{12}$ to $R^{16}$ represent alkyl radicals, they preferably contain 1 to 4 carbon atoms.

The radicals G are identical or different siloxane radicals of the following general formulae (VI) to (VIII)

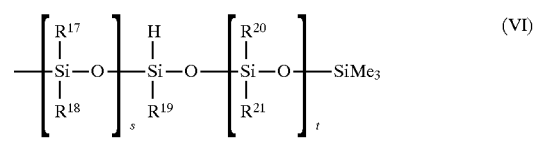

in which S and L in each case stand for a whole number from 0 to 8, with the proviso that the sum of s+t gives a value from 1 to 8, $R^{17}$ to $R^{20}$ in each case represent a methyl or phenyl group, with the proviso that $R^{17}$ and $R^{18}$ are the same or different when s assumes the value 2 or a higher value, and that the radicals $R^{20}$ are the same or different when t assumes the value 2 or a higher value, and $R^{21}$ represents a hydrogen atom or a methyl or phenyl group, with the proviso that the radicals $R^{21}$ are the same or different when t assumes the value 2 or a higher value, and Me stands for a methyl group,

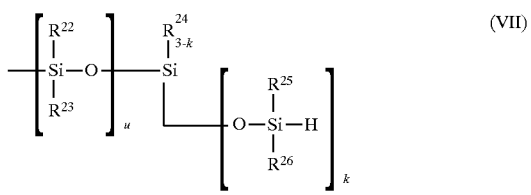

(VII)

in which u stands for a whole number from 0 to 8 and k stands for a whole number from 1 to 3, with the proviso that the sum of u+k assumes a value from 1 to 9, and $R^{22}$ to $R^{26}$ in each case represent a methyl or phenyl group, with the proviso that $R^{22}$ and $R^{23}$ are the same or different when u assumes the value 2 or a higher value, and that $R^{25}$ and $R^{26}$ are the same or different when k assumes the value 2 or a higher value, and

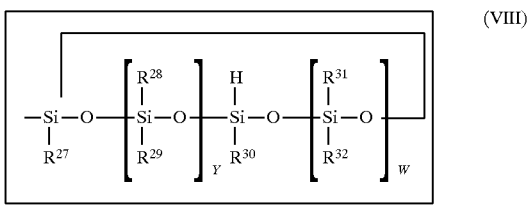

(VIII)

in which v and w in each case stand for a whole number from 0 to 4, with the proviso that the sum of v+w assumes a value from 1 to 4, $R^{27}$ to $R^{31}$ in each case represent a methyl or phenyl group, with the proviso that $R^{28}$ and $R^{29}$ are the same or different when v assumes the value 2 or a higher value, the radicals $R^{31}$ are the same or different when w assumes the value 2 or a higher value, and $R^{32}$ stands for a hydrogen atom, a methyl or phenyl group, with the proviso that the radicals $R^{32}$ are the same or different when w assumes the value 2 or a higher value.

The molecular weight of the SiH group-containing polyether preferably lies inn the range between 400 and 25,000.

Typical examples of SiH group-containing polyethers are given below:

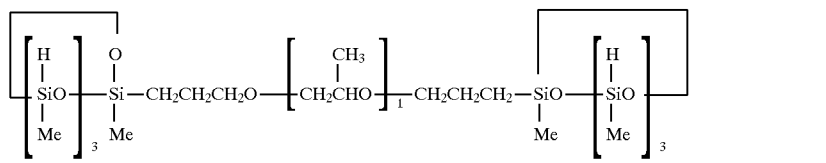

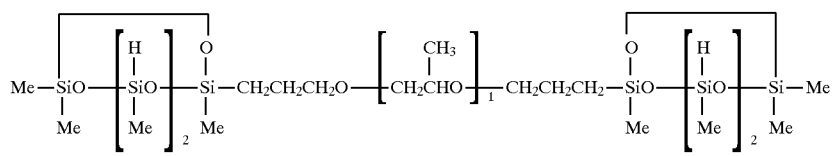

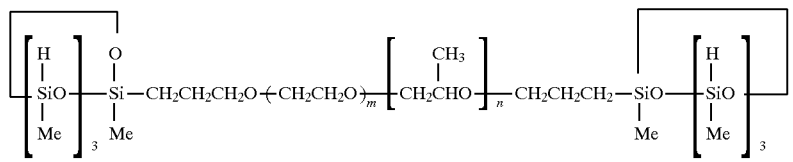

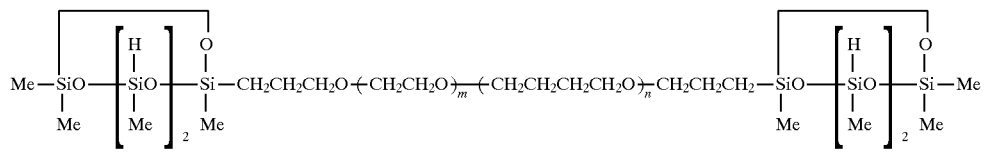

-continued
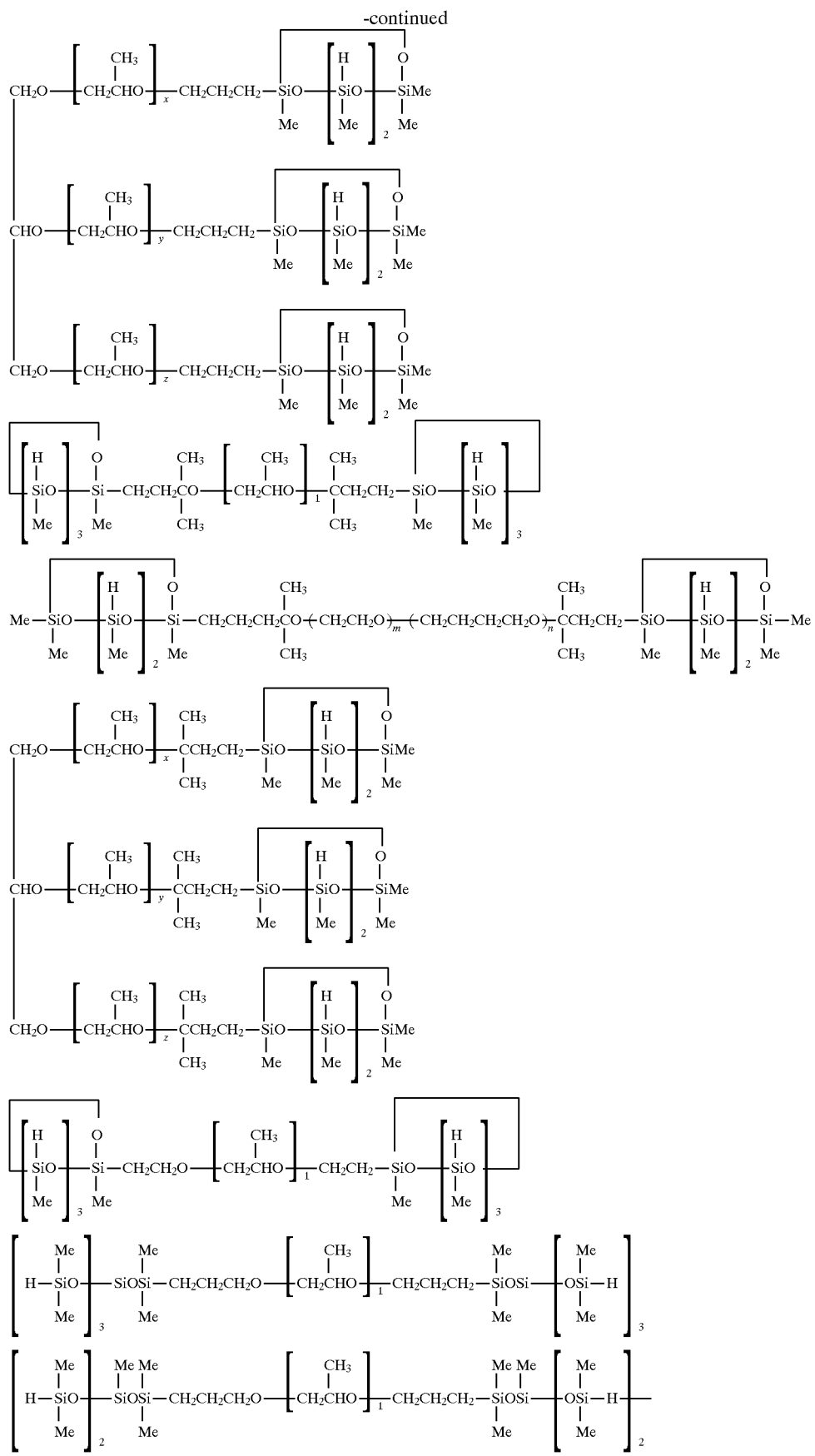

-continued

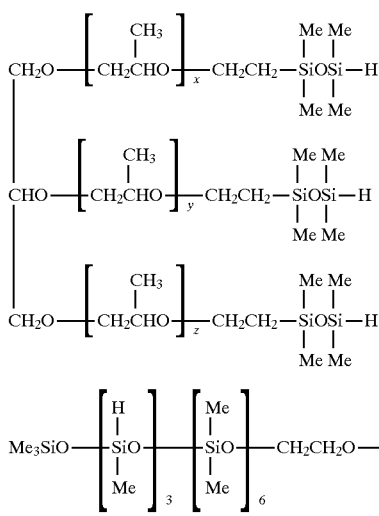

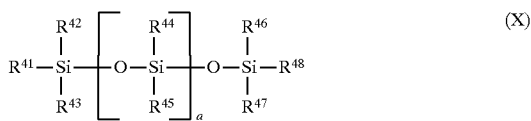

In the above-named formulae, l stands for a value from 30 to 60, and m, n, x, y and z in each case stand for a whole number of at least 1, with the proviso that the sum of m+n assumes a value from 3 to 60 and the sum of x+y+z assumes a value from 3 to 90, and Ph represents a phenyl group.

The production of thee SiH components is described in DE-A-40 19 249 and in DE-A-37 41 575, the disclosure of which in this respect is to be included here.

Also suitable as component (b) are SiH components which are described in DE-A-195 25 468, the disclosure of which is to be included here, and which are obtainable by reacting an at least difunctional acrylate or methacrylate compound with at least one mol per acrylate or methacrylate group of an at least difunctional SiH compound of the formulae

(X)

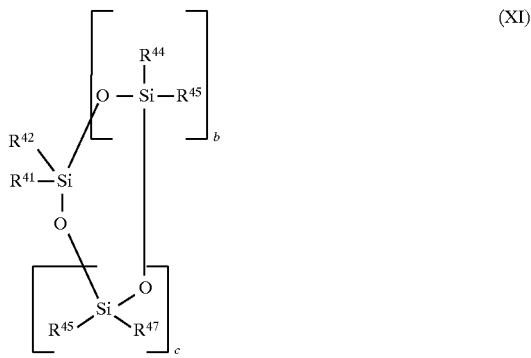

(XI)

in which
a=0 to 8,
b=0 to 8,
c=0 to 4 and
$R^{41}$ to $R^{48}$, which can be the same or different, stand for H or optionally halogenated hydrocarbon radicals form 1 to 18 carbon atoms per radical, in which at least two of the radicals $R^{41}$ to $R^{48}$ and at most six of these radicals stand for H, and b and c cannot be 0 at the same time, or

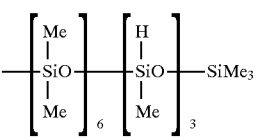

(XII)

in which
i=0 or 1 and
the radicals $R^{42}$, $R^{46}$ and $R^{47}$, which can be the same or different, stand for H or optionally halogenated hydrocarbon radicals with 1 to 18 carbon atoms per radical.

In the above formulae for the SiH compounds, the radicals $R^{41}$ are preferably H, $R^{42}$ and $R^{43}$ are preferably methyl. $R^{44}$ is preferably H, $R^{45}$, $R^{46}$ and $R^{47}$ are preferably methyl, $R^{48}$ is preferably H or Me. a is preferably 0 to 5, particularly 1 to 3. b is preferably 1 to 4, and c is preferably 0 to 2. i is preferably 0. Compounds of the following formulae are particularly preferred:

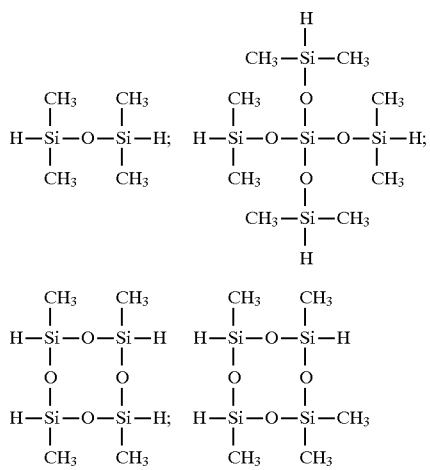

Suitable as di- or polyfunctional (meth)acrylate compounds for producing the SiH component (b) are the acrylic acid and methacrylic acid esters of di- or polyhydric alcohols such as ethylene glycol di(meth)acrylate, diethylene glycol di(meth)acrylate, triethylene glycol di(meth)acrylate, tetraethylene glycol di(meth)acrylate, butanediol di(meth) acrylate, hexanediol di(meth)acrylate, neopentyl glycol di(meth)acrylate, dodecanediol di(meth)acrylate, trimethylol propane tri(meth)acrylate and pentaerythritol tetra(meth)acrylate.

Also suitable are the (meth)acrylates of oligomeric or polymeric at least difunctional alcohols, e.g. polypropylene glycol, polybutylene glycol or polyethylene glycol di(meth)acrylate, or the (meth)acrylic acid esters of a copolymeric alcohol comprising propylene and ethylene oxide units or butylene and ethylene oxide units.

Also suitable are di- or polyfunctional (meth)acrylates with ester linkages such as, for example, the reaction product of 2-hydroxyethyl (meth)acrylate with phthalic or terephthalic acid or polycaprolactones with (meth)acrylate and end-groups. Also suitable are the (meth)acrylic acid esters of diols or polyols based on polycarbonates.

Also suitable are compounds of the bisphenol-A-di(meth)acrylate, bisphenol-A-diethyl (meth)acrylate and bisphenol-A-dipropyl (meth)acrylate and bisphenol-A-diglycidyl (meth)acrylate type. Also suitable are the derivatives, extended with alkoxide units, of the named bisphenol-A types, such as e.g. the diacrylic or dimethacrylic acid esters of bishydroxy polyalkoxybisphenol-A derivatives. Also suitable are the diacrylic and dimethacrylic acid esters, cited in DE-B-28 16 823, of bishydroxymethyltricyclo-(5.2.1.0$^{2,6}$)-decane, which can be extended with ethylene oxide or propylene oxide.

Also suitable are di- or polyfunctional (meth)acrylic acid amides, such as e.g. N,N'-methylene-bis(meth)acrylamide, N,N'-ethylene-bis(meth)acrylamide, N,N'-hexamethylene-bis(meth)-acrylamide, N,N'-isovalerylidene-bis(meth) acrylamide, 1,1',5,5' tetra(meth)acrylamido-n-pentane and the di- or polyfunctional (meth)acrylamides of at least difunctional secondary amines, such as e.g. 1,3-di-(4-piperidyl)-propane.

Urethane (meth)acrylates such as e.g. the reaction products of diisocyanates and hydroxyalkyl (meth)acrylates, as are described e.g. in DE A-23 12 559, can also be used. Mixtures of suitable monomers, or unsaturated polymers produced therefrom, can also be used.

The siloxane-substituted compounds can be produced according to conventional method or also analogously to DE-A 37 41 575. Production expediently takes place by reacting a di- or polyfunctional acrylate or methacrylate compound with a polyorganosiloxane which contains at least two SiH groups, using a platinum catalyst in a molar ratio of at least two SiH groups to one (meth)acrylate group. Since a content of platinum which remains after hydrosilylation decomposes the SiH component, residual platinum must be removed from the product in order to achieve adequate storage stability. In principle, the same methods can be used for this purpose as are described in DE-A-37 41 575, page 17, lines 20 to 35, e.g. by adsorption on diatomaceous earth or the like.

Usual polymerization inhibitors, e.g. 2,6-di-butyl-4-methylphenol or p-methoxyphenol, can be added to suppress polymerization of the (meth)acrylate during the hydrosilylation.

All catalysts which initiate hydrosilylation can be used as catalyst (c). Finely dispersed platinum, chloroplatinic acid or platinum complexes are for example suitable. Also suitable are all other compounds which are known for producing addition-crosslinking silicones. Catalysts of finely dispersed platinum are described for example in U.S. Pat. No. 2,970,150 and are preferably used in very finely dispersed form. Chloroplatinic acid catalysts are described in U.S. Pat. No. 2,823,218 and are preferably used in a solution in an alcohol, ketone, ether or hydrocarbon. Suitable platinum complexes are platinum/olefin complexes, such as are described in U.S. Pat. Nos. 3,159,601 and 3,159,662. Preferred platinum complexes are platinum/vinyl siloxane complexes, in particular platinum/divinyl tetramethyl disiloxane complexes, such as e.g. the reaction product of platinum halides, such as e.g. chloroplatinic acid with a vinyl group-containing polysiloxane or tetramethyl disiloxane such as are described in U.S. Pat. No. 3,775,452 or U.S. Pat. No. 3,814,780.

Linear or branched organopolysiloxanes which contain at least two alkenyl groups/molecule bound to silicon atoms can be used as component (e). The units of the organopolysiloxane can be represented by the following formula:

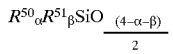

in which $R^{58}$ stands for an alkenyl group with 1 to 10 carbon atoms, $R^{51}$ stands for a single-bond hydrocarbon group with 1 to 10 carbon atoms, and the letters $\alpha$ and $\beta$ stand for positive numbers which satisfy the condition $0 \leq \alpha < 4$, $0 \leq \beta < 4$ and $0 \leq \alpha + \beta < 4$, so that the organopolysiloxane has at least two alkenyl groups.

Examples of $R^{50}$ are vinyl, allyl, methyl vinyl, propinyl, butinyl, pentenyl and hexenyl groups as well as also cyclic unsaturated hydrocarbons such as e.g. cyclopropenyl, cyclobutenyl, cyclopentenyl and cyclohexenyl groups.

The hydrocarbon group $R^{51}$ contains alkyl groups, such as methyl, ethyl, propyl, butyl or aryl groups such as e.g. phenyl, aralkyl groups such as e.g. benzyl, and cycloalkyl groups such as e.g. cyclohexyl. The groups $R^{51}$ can be substituted, provided that the substitution does not impair the curability of the mixture. For example, the alkyl groups can have halogen substituents, such as e.g. trifluoropropyl.

Diorgnopolysiloxanes with terminal triorganosiloxy groups, of which at least one of the three organic groups is a vinyl group, are preferred as component (e). Preferred diorganosiloxanes of this structure are described by the following formula:

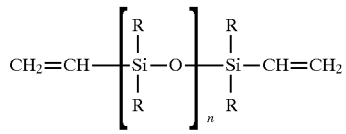

in which R represents an unsubstituted or substituted monovalent hydrocarbon group with 1 to 10 carbon atoms which is preferably free of aliphatic multiple bonds, and n is a whole number. The radicals R can be the same or different. At least 50% up to 100% of the radicals R are preferably methyl groups, and examples of other R groups are ethyl, phenyl, vinyl and 3,3,3-trifluoropropyl groups. The value of n is to be such that at 25° C. the polymer has a viscosity of between 100–300,000 mPa.s, preferably between 500 and 100,000 mPa.s. Such molecules are described in U.S. Pat. No. 4,035,453, the disclosure of which in this respect is to be included here. The production of component (d) takes place according to usual processes which are described e.g. in W. Noll Chemie und Technologie der Silikone, Verlag Chemie, Weinheim, 2nd Edition 1964, pages 162–206 or J. Burghardt, Chemie und Technologie der Polysiloxane in "Silikone, Chemie und Technologie", Vulkanverlag, Essen, 1989, pages 23–37.

$\alpha,\omega$-Dimethylvinylsiloxy-terminated polydimethylsiloxanes of the following structure with a viscosity of 100 to 300,000 mPa.s, preferably 500 to 100,000 mPa.s, are particularly preferred:

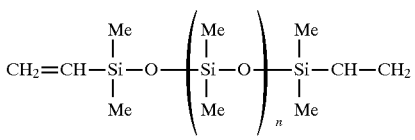

α,ω-Dimethylvinylsiloxy-terminated dimethylsiloxane/methylphenylsiloxane copolymers and α,ω-dimethylvinylsiloxy-terminated dimethylsiloxane/diphenylsiloxane copolymers as well as α,ω-vinylphenylmethylsiloxy-terminated polydimethylsiloxanes are also particularly preferred, what was said above applying for their viscosity in relation to the index n.

Polysiloxanes of the following structure, in which the radicals R can be the same or different and are defined as above, are also preferred:

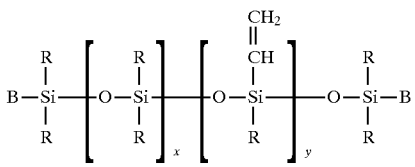

with the proviso that B can be equal to R or vinyl and $0<y/(x+y)<0.3$. For B equals vinyl, y is a whole number with a value greater than or equal to 1. For B equals R, y is a whole number greater than or equal to 3. The sum of x+y is to be such that the viscosity at 25° C. lies between 100 and 300,000 mPa.s, preferably between 500 and 100,000 mPa.s. Particularly preferably, R equals methyl and B equals methyl and $0<y/(x+y)<0.1$.

Also suitable are vinyl-terminated polysiloxanes with the following T-shaped structure:

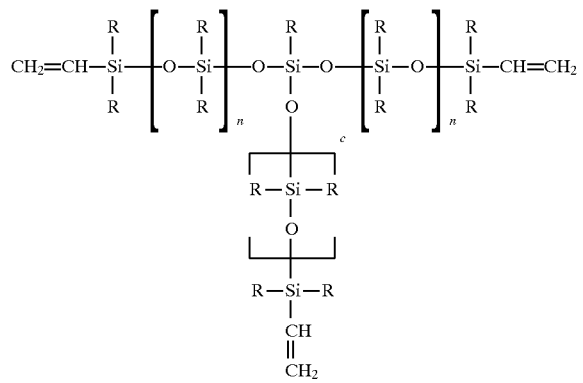

in which the radicals R are as defined above. Preferred radicals R and preferred viscosity ranges are as defined above. The radical R particularly preferably equals methyl. n can be the same or different and has the above meaning.

Mixtures of different components (e) can also be used.

The vulcanization of the impression compositions according to the invention takes place by an addition reaction in which SiH groups react with unsaturated groups of the polyether component and of the polyorganosiloxane component. The molar ratio of component (b) to component (a) is expediently to be chosen such that the quantity of SiH groups in component (b) is 0.5–10 mol per 1 mol of the alkenyl radicals of component (a). The quantity of SiH groups is preferably 0.8–5 mol, particularly preferably 0.9–3 mol, per 1 mol of the alkenyl radicals of (a).

The quantity of component (e) is expediently to be chosen such that the proportion of component (e) is 0.01 to 50 wt. %, preferably 0.1 to 30 wt. % and particularly preferably 0.1 to 20 or 0.1 to 15 wt. % or 1 to 10 wt. %, relative to the total weight of components (a) to (e). The ratio of the sum of the percentages by weight of components (a)+(b) to the percentage by weight of component (e) is expediently at least 1:1, preferably at least 2:1, particularly preferably at least 3:1 or at least 5:1. The hydrophilia of the total mixture introduced by the polyether portions thereby remains guaranteed.

The quantity of platinum catalyst (c) used is preferably 0.1 ppm–5000 ppm, in particular 0.1–1000 ppm, relative to the total weight of components (a), (b) + (e).

The optionally present usual additives are present in a total quantity of at most 80 wt. %, preferably at most 70 wt. % and in particular at most 60 wt. %, relative to the total weight of the impression material.

To set the processing conditions, in particular the flowability and hardness of the finished mould, the impression material optionally contains usual inorganic and/or organic fillers as component (d). Suitable inorganic fillers are e.g. pyrogenic silicon dioxide, diatomaceous earth, silica gel, quartz powder, ground glass fibres, titanium dioxide, aluminium oxide, magnesium oxide, calcium carbonate and mica. The grain distribution of the fillers used is preferably selected such that no fillers whatsoever with grain sizes >50 μm are included; the maximum grain size is preferably 25 μm, particularly preferably 5 μm. Depending on the intended use, the quantity of fillers is 0–80 wt. %, preferably 5–50 wt. %, relative to the total weight of the impression material.

The fillers can be coated. Silane-coated fillers are advantageous. Suitable as silanes are the silanes known to be used for coating fillers. For example, hexamethyldisilazano and divinyl tetramethyldisilazane are particularly suitable. The fillers can be made hydrophobic by treatment with organosilanes or siloxanes or by etherification of hydroxyl groups to alkoxy groups. One type of filler can be used, but a mixture of at least two fillers can also be used. Furthermore, the mixture according to the invention can contain additives such as platicizers, pigments, antioxidants, release agents and the like.

Suitable as platicizer are compounds such as tributyl citrate, dibenzyl toluene, polyethylene oxides and the copolymers of ethylene and propylene oxide. The hardness of the vulcanization product obtained can also be reduced by adding a suitable quantity of a silicone oil or of an oligomeric or polymeric ether with an alkenyl group, such as e.g. a vinyl or allyl group, to one end, or a silicone oil with non-functional groups, such as e.g. trimethylsiloxy-end-stopped polydimethylsiloxanes. The quantity of plasticizer is preferably 0–40 wt. %, particularly preferably 0–20 wt. %, relative to the total weight. A hydrophilizing agent can optionally be added to regulate the hydrophilia of the compositions according to the invention. Suitable hydrophilizing agents are for example the hydrophilic silicone oils, fluorinated hydrocarbon compounds, ethoxylated alcohol derivatives, ethoxylated alkyl phenols, ethoxylated amines and block copolymers of propylene oxide and ethylene oxide described in DE A 43 06 997. Also suitable are polyether carbosilanes which are described in DE-A-44 33 139.8.

Since the number of SiH groups to guarantee a rapid setting is relatively large compared with the quantity of unsaturated radicals in the curable impression material, hydrogen gas can be released as a by-product during setting. In order not to thereby influence the dimensional stability, an absorber for hydrogen gas is preferably used. Metal powders of palladium, platinum, nickel, magnesium or zinc are suitable; particularly suitable are carrier materials provided with such metals, for example silica gel coated with palladium or calcium carbonate coated with palladium.

In the following examples and test examples, a SiH component was used which was prepared as follows according to the teaching of DE-A-38 38 587.

7 mg of hexachloroplatinic acid are added to 7.92 g of bisallyloxyethyl ether of bisphenol A (20 mmol), and the mixture is stirred for 15 min at room temperature until most of the hexachloroplatinic acid has dissolved. 9.6 g of tetramethyl cyclotetrasiloxane (40 mmol) are then added slowly dropwise at room temperature. The mixture heats up to a temperature of 55° C. within 20 min. Stirring continues until the mixture has cooled down again to a temperature of 30° C., and stirring continues for a further 2 h. It is then drawn off by suction from slightly black precipitate over diatomaceous earth and 10 g of a SiH compound are obtained. The $^1$H-NMR spectrum of the substance showed no more allyl groups.

EXAMPLE 1

A firm base paste was obtained by kneading 5.1 parts by weight of one of the above-described SiH components, 63.6 parts by weight of a diallyl ether of a polypropylene glycol with an average molecular weight of 4000, 6.5 parts by weight of silanized pyrogenic silicic acid and 24.8 parts by weight of a silanized quartz powder.

67.8 parts by weight of a α,ω-vinyldimethylsiloxy-terminated polydimethylsiloxane with a viscosity of 2000 mPa.s were mixed in a kneader with 0.6 parts by weight of a platinum catalyst consisting of platinum-tetramethyl divinyl disiloxane complex. A firm catalyst paste was obtained by adding 6.4 parts by weight of silanized pyrogenic silicic acid, 24.8 parts by weight of silanized quartz powder and 0.4 parts by weight of a hydrogen absorber.

Base and catalyst pastes were subjected to a storage-stress test, by being stored in each case at 23° C., 36° C. and 50° C. After specific time periods (see Table 1), samples were taken in each case and made to set in a weight ratio of 5 parts of base paste to one part of catalyst paste, an elastic rubber being the result in each case. The processing time represents the moment of onset of vulcanization.

TABLE 1

Stress test of base and catalyst pastes

| Storage time | Storage temperature | Processing time |
| --- | --- | --- |
| Start |  | 4 min 00 sec |
| 1 month | 23° C. | 4 min 00 sec |
|  | 36° C. | 4 min 00 sec |
|  | 50° C. | 4 min 00 sec |
| 3 months | 23° C. | 3 min 45 sec |
|  | 36° C. | 4 min 00 sec |
|  | 50° C. | 4 min 00 sec |

COMPARATIVE EXAMPLE 1

A base paste was made analogously to the above production process by kneading 8.2 parts by weight of the above described SiH component, 46.5 parts by weight of a diallyl ether of polypropylene glycol 4000, 9.4 parts by weight of silanized pyrogenic silicic acid and 35.8 parts by weight of a silanized quartz powder. A catalyst paste was made by kneading 54.4 parts by weight of PPG 4000 diallyl ether, 0.2 parts by weight of platinum-tetramethyl divinyl disiloxane complex, 0.15 parts by weight of a hydrogen absorber, 9.4 parts by weight of silianized pyrogenic silicic acid and 35.9 parts by weight of a silanized quartz powder.

Samples of the two pastes were mixed together in the weight ratio of 1:1 and resulted in an elastic rubber in a fast vulcanization. Analogously to the procedure of Example 1, base and catalyst pastes were stored at 23° C., 36° C. and 50° C. After storage was complete, the following stability sequence resulted (See Table 2):

TABLE 2

| Storage time | Storage temperature | Processing time |
| --- | --- | --- |
| Start |  | 3 min 00 sec |
| 1 month | 23° C. | 2 min 30 sec |
|  | 36° C. | no setting |
|  | 50° C. | no setting |

The base and catalyst pastes stored at 36° C. and 50° C. were examined separately. Analogously to the above production stipulation, in each case a fresh base and catalyst paste was made again, in which vulcanization set in after mixing and after a processing time of 3 min. When fresh catalyst paste was mixed with the base pastes stored at 36° C. and 50° C., the result was a vulcanization which set in after a processing time of ca 3 min, which means that the base paste had remained stable at 36° C. and 50° C.

Mixing of fresh base paste with catalyst paste stored at 36° C. and 50° C. led to a mixture product which no longer cured. This shows that the catalyst paste had lost its ability to function while in storage. This also shows that the polyether-containing catalyst paste of the Comparative Example has a far poorer storage stability than the catalyst according to the invention of Example 1 in which it was not polyether, but vinyl-terminated polydimethylsiloxane, which served as paste base.

EXAMPLE 2

A base paste was produced by kneading 5.6 parts by weight of a compound analogous to component 1, 45.8 parts by weight of PPG 4000 diallyl ether, 4.7 parts by weight of silanized pyrogenic silicic acid, 2 parts by weight of a surface-active substance, 1.7 parts by weight of a colour paste consisting of dye and plasticizer and 40.3 parts by weight of silanized quartz powder. A related catalyst paste was made by kneading together 15.2 parts by weight of a trimethylsiloxy-terminated polydimethylsiloxane with a viscosity of 50 mPa.s, 39.8 parts by weight of a α,ω-vinyldimethylsiloxy-terminated polydimethylsiloxane with a viscosity of 2000 mPa.s, 8.3 parts by weight of a platinum-vinyl siloxane complex catalyst (platinum content 1.3%), 0.07 parts by weight of a hydrogen absorber, 4.6 parts by weight of pyrogenic silanized silicic acid and 31.9 parts by weight of a silanized quartz powder. The catalyst and base pastes were mixed together in the weight ratio of 1:4, the result being a vulcanization product which was characterized as follows (see column A values in Table 3):

TABLE 3

|  | A | B |
| --- | --- | --- |
| Remaining deformation | 1.0% | 2.15% |
| Elastic mouldability | 10.8% | 11.0% |
| Tensile strength | 1.1 mPa | 0.5 mPa |
| Tensile elongation at break | 60% | 24% |
| Comments | Elastic, | Inhomogeneous |

TABLE 3-continued

| A | B |
|---|---|
| homogeneous rubber | product; individual layers separable from one another; "puff pastry" |

COMPARATIVE EXAMPLE 2

As a comparison, a second catalyst paste was made analogously to the above production example, but the α,ω-vinyl dimethylsiloxy-terminated polydimethylsiloxane was replaced by a trimethylsiloxy-terminated dimethyl silicone oil of the same viscosity and quantity. The values in Table 3, column B resulted on setting with the base paste analogously to Example 2.

The values for compression deformation and for recovery after deformation were determined in accordance with ISO 4823. The values for tensile strength and extensibility were determined by tensile strength tests in a Zwick 1435 universal test machine. Cylindrical test pieces with a length of 50 mm and a diameter of 6 mm were produced according to DIN standard 50125, form B. For this purpose, base and catalyst components were mixed together homogeneously in the defined mixture ratio, and poured into two brass half-moulds in accordance with DIN 50125 (form B). The half-moulds were placed together and the test pieces were removed after 10 min at 23° C. The test pieces were stored for a further 24 hours at 23° C. and 50% relative humidity and then torn between testing jaws of the Zwick apparatus. Evaluation of the calibration curve gave the values for extensibility (tensile elongation at break) and tensile strength.

The surface hardness of the set rubber of Example 2, measured in Shore-A hardness units according to DIN 53 505, 24 hours after setting is complete is 44, whereas measurement of the surface hardness of Comparative Example 2 was meaningless, because of the inhomogeneity. The values in Table 3 prove that the vinyl-terminated polydimethylsiloxane together with the diallyl ether of polypropylene glycol contributes to the improvement in the rubber structure, whereas the dimethyl silicone oil (column B) adversely affects the rubber properties.

We claim:

1. An addition-crosslinking polyether impression material which contains (a) a polyether which has two or more optionally substituted vinyl and/or allyl end-groups,
   (b) a SiH component,
   (c) a platinum catalyst,
   (d) optionally usual additives, and characterized in that it additionally contains
   (e) an organopolysiloxane with two or more alkenyl groups.

2. A polyether impression material according to claim 1, characterized in that the units of the organopolysiloxane of component (e) have the following formula:

$$R^{50}{}_\alpha R^{51}{}_\beta SiO_{\frac{(4-\alpha-\beta)}{2}}$$

in which $R^{50}$ stands for an alkenyl group with 1 to 10 carbon atoms and $R^{51}$ stands for a single-bond hydrocarbon group with 1 to 10 carbon atoms, and the letters α and β stand for positive numbers which satisfy the condition $0 \leq \alpha < 4$, $0 \leq \beta < 4$ and $0 \leq \alpha + \beta < 4$.

3. A polyether impression material according to claim 1 or 2, wherein the organopolysiloxane of component (e) has the following formulae:

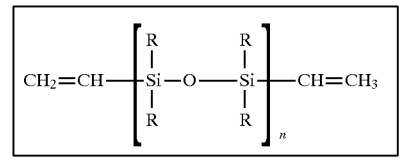

and/or

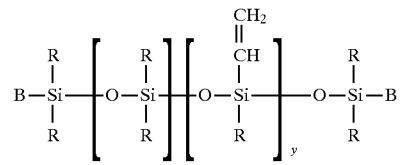

and/or

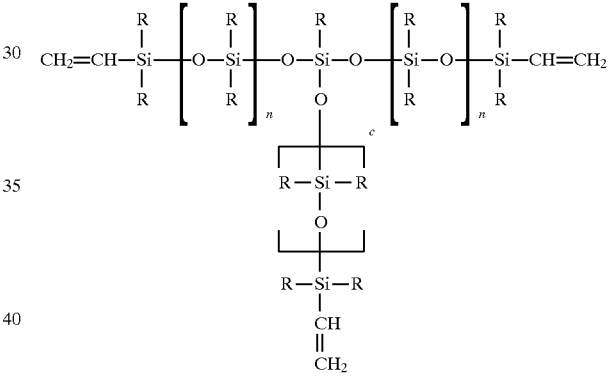

in which R represents an unsubstituted or substituted monovalent hydrocarbon group with 1 to 10 carbon atoms which is preferably free of aliphatic multiple bonds, n represents a whole number, B equals R or stands for vinyl and $0 < y/(x+y) < 0.3$, in which y is a whole number greater than or equal to 1 when B stands for vinyl, and y is a whole number greater than or equal to 3 when B stands for R.

4. A polyether impression material according to claim 3, wherein 50% to 100% of the radicals R are methyl groups and the other radicals R are selected from ethyl, phenyl, vinyl and 3,3,3-trifluoropropyl groups.

5. A polyether impression material according to claim 3, wherein n, x and y are selected such that at 25° C. the polymer has a viscosity of from 100 to 300,000 mPa.s.

6. A polyether impression material according to claim 1, wherein the molar ratio of component (b) to component (a) is selected such that the quantity of SiH groups in component (b) is 0.5–10 mol per 1 mol of the alkenyl radicals of component (a).

7. A polyether impression material according to claim 1, wherein the proportion of component (e) is 0.01 to 50 wt. % relative to the total weight of components (a) to (e).

8. A polyether impression material according to claim 1, wherein the catalyst is contained in a quantity of 0.1–5000 ppm, relative to the total weight of components (a), (b) + (e).

9. A polyether impression material according to claim 1, wherein the optionally present additives according to component (d) are present in a total quantity of at most 80 wt. %, relative to the total weight of the impression material.

10. A polyether impression material according to claim 1, in a two-part form, with the proviso that the components (b) and (c) are spatially separated from each other.

11. A polyether impression material according to claim 1, in two-part form, the components (a) and (b) being mixed to form a base paste and the components (c) and (e) being mixed to form a catalyst paste, and the optionally present component (d) being present either in the base paste or in the catalyst paste or in both.

12. A method of producing a dimensionally stable jaw impression, comprising the step of forming a negative impression meterial in a patient's mouth with a dental impression material that is an addition-crosslinking polyether impression material containing:

(a) a polyether which has two or more optionally substituted vinyl and/or allyl end-groups, (b) an SiH component, (c) a platinum catalyst, (d) optionally usual additives, and (e) an organopolysiloxane with two or more alkenyl groups.

13. A polyether impression material as recited in claim 5, wherein the polymer has a viscosity of from 500 to 100,000 mPa's.

14. A polyether impression material according to claim 6, wherein the quantity of SiH groups in component (b) is 0.8–5 mol of the alkenyl radicals of component (a).

15. A polyether impression material according to claim 6, wherein the quantity of SiH groups in component (b) is 0.9–3 mol per 1 mol of the alkenyl radicals of component (a).

16. A polyether impression material according to claim 7, wherein the proportion of component (e) is 0.1 to 20 wt. %, relative to the total weight of components (a) to (e).

17. A polyether impression material according to claim 7, wherein the proportion of component (e) is 0.1 to 20 wt. %, relative to the total weight of components (a) to (e).

18. A polyether impression material according to claim 7, wherein the proportion of component (e) is 0.1 to 15 wt. %, relative to the total weight of components (a) to (e).

19. A polyether impression material according to claim 8, wherein the catalyst is contained in a quantity of 0.1 to 1000 ppm, relative to the total weith of components (a), (b) and (e).

20. A polyether impression material according to claim 9, wherein the optionally present additives according to component (d) are present in a total quantity of at most 70 wt. %.

21. A polyether impression material according to claim 9, wherein the optionally present additives according to component (d) are present in a total quantity of at most 60 wt. %.

* * * * *